United States Patent [19]

Weibel

[11] Patent Number: 5,008,254

[45] Date of Patent: Apr. 16, 1991

[54] SUGAR BEET PECTINS AND THEIR USE IN COMESTIBLES

[76] Inventor: Michael K. Weibel, 120 Gallows Hill Rd., Redding, Conn. 06896

[21] Appl. No.: 430,166

[22] Filed: Nov. 1, 1989

Related U.S. Application Data

[63] Continuation-in-part of Ser. No. 334,596, Apr. 6, 1989, Pat. No. 4,923,981, which is a continuation-in-part of Ser. No. 62,445, Jun. 15, 1981, abandoned, which is a continuation-in-part of Ser. No. 512,940, Jul. 12, 1983, Pat. No. 4,831,127, which is a continuation-in-part of Ser. No. 414,931, Sep. 3, 1982, abandoned.

[51] Int. Cl.$^5$ .................. C08B 37/06; A61K 31/725; A21D 2/18
[52] U.S. Cl. .......................... 514/57; 536/2; 536/56; 514/54; 514/777; 514/781; 424/439; 424/441; 426/570; 426/602; 426/605; 426/615; 426/804
[58] Field of Search .............. 536/2, 56; 514/54, 777, 514/781, 57; 424/439, 441; 426/602, 605, 615, 804, 570

[56] References Cited

U.S. PATENT DOCUMENTS

| | | | |
|---|---|---|---|
| 3,023,104 | 2/1962 | Battista | 426/660 |
| 4,629,575 | 12/1986 | Weibel | 536/128 |
| 4,672,034 | 6/1987 | Rombouts et al. | 536/2 |
| 4,737,582 | 4/1988 | Goldman et al. | 536/2 |
| 4,831,127 | 5/1989 | Weibel | 536/56 |
| 4,875,974 | 10/1989 | Rich | 536/2 |

Primary Examiner—Ronald W. Griffin
Attorney, Agent, or Firm—Lieberman Rudolph & Nowak

[57] ABSTRACT

Sugar beet pectins are provided, which are characterized by unique properties which render them particularly useful in the preparation of food or drug comestibles. By incorporating the sugar beet pectins into food or drug products, improved properties, including physicochemical, rheological and nutritional properties are obtained.

29 Claims, No Drawings

SUGAR BEET PECTINS AND THEIR USE IN COMESTIBLES

CROSS-REFERENCE TO RELATED APPLICATIONS

This application is a continuation-in-part of U.S. Pat. application Ser. No. 334,596, filed Apr. 6, 1989, now U.S. Pat. 4,923,981, which is a continuation-in-part of Ser. No. 062,445, filed June 15, 1987, now abandoned. Ser. No. 062,445 is a continuation-in-part of Ser. No. 512,940 filed July 12, 1983, now U.S. Pat. No. 4,831,127 which, in turn, is a continuation-in-part of U.S. patent application Ser. No. 414,931, now abandoned, filed Sept. 3, 1982. Each of the foregoing applications is incorporated herein by reference.

BACKGROUND OF THE INVENTION

1. Field of the Invention

This invention relates in general to sugar beet pectins. In one aspect, this invention is directed to a pectin extract obtained from sugar beet. In another aspect, this invention relates to sugar beet pectin having utility in comestibles.

2. Background of the Related Art

Spent sugar beet pulp consists largely of structural polysaccharide complexes associated with the primary cell wall of parenchymatous tissue. This tissue has been subjected to an exhaustive hot water extraction to remove sugar and other intracellular constituents. Subsequent extraction of spent beet pulp under hydrolytic conditions generates solubilized forms of the non-cellulosic components whose yield and chemical classification vary depending on the severity of hydrolysis condition and the specific extractive method employed. Past reports tended to segregate the solubilized polysaccharides into largely neutral carbohydrate complexes (hemicelluloses) and acidic carbohydrate complexes (pectins). More recent investigations suggest that both the neutral and acidic carbohydrates may be covalently associated components of the non-cellulosic structural macropolysaccharides compromising the cell wall of parenchymatous plant tissue. These reports imply that hemicellulose or pectin isolates represent highly heterogeneous fragments resulting from natural or induced hydrolysis occurring during their preparation. (F. M. Rombouts and J. F. Thibault, "Sugar Beet Pectins: Chemical Structure and Gelation Through Oxidative Coupling" in *Chemistry and Function of Pectins*, pp. 49–60, 1986, edited by M. L. Fishman and J. J. Jen, ACS, Washington, D. C.; I.C.M. Dea and J. K. Madden, "Acetylated Pectic Polysaccharides of Sugar Beet" in *Food Hydrocolloids*, Vol. 1, pp. 71–88, 1986; L. Phatak, K. C. Chang and G. Brown, "Isolation and Characterization of Pectin in Sugar Beet Pulp" in *J. of Food Science*, Vol. 53, pp. 830–833, 1988). These and other investigators postulate a rhamnogalacturonide backbone with neutral sugar appendages composed largely of arabinogalactan emanating from the backbone in clusters along the chain. Several types of ester functionality are present — the uronic acid component of the backbone is highly esterified as the methylester feruloyelster groups are believed to be located on the neutral carbohydrate appendages and a substantial degree of acetyl ester function is present which cannot at present be assigned to either pendant or backbone structure (or both). For descriptive purpose associated with the specification of this invention and the appended claims, the polysaccharide complex isolated by extractive hydrolysis of spent sugar beet pulp as described herein will be referred to as a pectin, or modified pectin.

Commercial pectins are derived from citrus and apple pulps. They are characterized by high viscosity of low solids aqueous solutions and form gels in the presence of high solids sucrose solutions under mildly acidic conditions. Commercial pectins derived from other plant sources have long been sought. Commercial pectin production from sugar beet commenced in Europe during World War II but ceased when citrus and apple pulps again became available. Sugar beet pectins were generally of inferior jelly grade and their function was enhanced by conversion to low ester pectinic acids which produce ionically crosslinked gels in the presence of polyvalent cations (R. H. McDowell, U.K. Patent 555,842, Sept. 9, 1943). Probably because of a preoccupation with commercial pectin replacement in jams, jellies and gels which still persists (F. M. Rombouts, J. F. Thibault and C. Merrier, French Patent 8,307,208, 1983) there has been virtuallY no other commercial use of this interesting hydrocolloid complex. While others have commented academically on potential application based on chemical or physical characterization, there has been no reduction to practice of any use of beet pectin other than that of its use as a gel forming additive in fruit spreads.

Moreover, prior to the present invention, there was no process available which utilized a plug flow reactor to achieve hydrolytic extractions which provide a sugar beet pectin having properties which extended their scope of utility beyond jams, jellies and similar fruit spreads.

Accordingly, one or more of the following objects can be achieved by the practice of the present invention. It is an object of this invention to provide a sugar beet pectin extract having utility in comestibles. Another object of this invention is to provide a sugar beet pectin extract having characteristics not possessed by commercially available pectin products. A further object of this invention is to provide sugar beet pectins having applications in comestibles other than in fruit spreads. Another object of this invention is to provide sugar beet pectins having emulsion stabilizing properties for comestibles, such as flavor oils, vegetable oils, dairy products and the like. A further object is to provide sugar beet pectins which supply a source of soluble dietary fiber which can be added to comestibles. A still further object is to provide sugar beet pectins which can replace loss of texture or mouth feel when sugar substitutes are used in the preparation of comestibles. A further object is to provide a non-hydroscopic adhesive or film former for binding granulated or extruded food products. These and other objects will be readily apparent to those skilled in the art in the light of the teachings herein set forth.

SUMMARY OF THE INVENTION

In the broad aspect, the present invention is directed to sugar beet pectins, their use in comestibles such as food and drugs, and the comestibles obtained therefrom, other than fruit spreads.

DETAILED DESCRIPTION OF THE INVENTION

It has been discovered that pectins derived from high temperature, controlled hydrolytic aqueous extraction of spent sugar beet pulp, provide a new class of hydrocolloids which have important application as functional additives and ingredients in comestibles other than gel functionality desired for jams and jellies. Specifically, beet pectins, prepared by this process, provide unusual emulsion stabilizing properties for flavor oils, vegetable oils and dairy products; a source of soluble dietary fiber which can be added to comestibles in sufficient amount to allow nutritional labeling claims without imparting undesirable properties to the food; a water binding or solids functionality in reduced caloric or dietetic foods where significant loss of texture or mouth feel results from replacement of sugar, dextrose or syrup solids with high intensity sweeteners; and a nonhydroscopic adhesive or film former for binding granulated or extruded food products and encapsulated or co-dried powders, respectively.

The method of the present invention relies on thermomechanical manipulation of the spent pulp under mildly acidic conditions whereby the hemicellulose complex becomes solubilized. In the case of sugar beet pulp the extracted complex is composed of high molecular weight polysaccharides whose composition is largely L-arabinose, D-galactose and D-galacturonic acid. The generic term for the dominant polysaccharide is "pectin". Pectin derived from sugar beet is very different from that isolated from other types of plant tissue such as citrus pulp. Beet pectin is highly acetylated and contains a moderate degree of feruloyl ester substitution. These relatively hydrophobic moieties coupled to extensive methyl esterification of D-galacturonic acid appear to generate lipophilic domains within an otherwise hydrophilic macromolecule. Ester functionality such as that to be found in beet pectin ordinarily undergoes facile hydrolysis so that while limited hydrolysis is needed to elicit solubilization and extraction, extensive hydrolysis leading to loss of ester functionality is not usually desired.

It has been discovered that aqueous extracts of spent sugar beet pulp, a by-product of sugar beet refining, display unusual properties with respect to emulsification and emulsion stabilization of oleaginous substances in water. These desirable properties appear to be controlled by the extent or degree of hydrolytic processing which occurs during extraction. Moreover, the beet pectins prepared by the aforementioned process possess properties which distinguish them from sugar beet pectins previously known.

Flavor emulsions are one type of oil-in-water emulsions prepared for the food industry. Citrus oils and many other beverage flavoring agents are used with gum arabic as an emulsion stabilizer. It is believed that gum arabic effects emulsion stability by the formation of a protective film around each dispersed oil particle. In addition to steric prevention of coalescence, the gum is believed to influence the hydrodynamic size and density of the colloidal oil particles rendering their specific gravity close to that of the continuous phase in which they remain permanently suspended even after high dilution. This property is the basis of "cloud stabilization" used to impart a uniform cloudy character to imitation fruit beverages. While other plant derived hydrocolloids have been considered for these purposes, none have thus far been found which match the superior performance of gum arabic.

It has been discovered that the pectin complex from beet is an exceptional emulsifier and emulsion stabilizer for citrus flavor oils, particularly those which are useful in beverages. Concentrated flavor oil emulsions containing 10–30% oil w/w can be generated by ultrasonic dismembrators, impact discharge devices (submerged jet type — Microfluidies Corp., Newtown, Mass. or annular orifice discharge — Gaulin Corp., Everette, Mass.) and high speed rotor/stators generators in the presence of 1 to 40% w/w beet pectin. These master emulsions can be further diluted 50 to 100 fold to produce buoyantly stable, homogeneous dispersions of the flavor oil highly desired by the beverage industry.

In addition to liquid emulsion concentrates, flavor oils are frequently encapsulated by co-spray drying a flavor oil in the presence of a film forming agent such as maltodextrin. Typically this application produces a free flowing, dry powder that can be conveniently stored and dispensed. Two component functions for the aqueous phase are required — an emulsion stabilizer and a film former. The latter is preferably a material that generates low viscosities at high solids content. Only one material of natural origin is known today which can fulfill both roles — gum arabic. No natural alternatives are known and replacement systems generally contain a hydrophobically modified starch (stabilizer) and a maltodextrin or hydrolyzed gelatin (film forming carrier). Certain modified starches can provide both functional requirements. It has now been found that sugar beet pectin is useful in flavor encapsulation and provides an excellent vehicle for spray drying flavors, food additives such as vitamin E, B-carotene and certain pharmaceuticals.

Other emulsions and emulsion applications will become apparent to those skilled in the art. For example, it has long been an objective of food manufacturers to provide margarine and butter spreads which are fluid and "pumpable" at refrigerated temperatures. Today's products are blends of various oils, fats and waxes which are designed to have a relatively low solidification temperature. Hence, such products become very thin and runny at ordinary room temperature. Sugar beet pectin easily emulsifies such materials and provides a relatively temperature independent rheology regardless of the melting point of the dispensed oleaginous phase. Other dairy type applications are believed to also benefit by employing sugar beet pectins in products such as ice creams, cheese spreads, and the like.

Vegetable derived extracts, specifically guar gum and fruit pectins, and gums isolated from grain brans, such as barley and oats, which are largely B-glucans have been found to promote lowering of plasma cholesterol and lipids. These sources of "soluble" fiber, i.e., they represent acid or alkali solubilized components of particulate, fibrous plant matter, are believed to have beneficial health effects when included in the diet (*The Physiological Effects and Health Consequences of Dietary Fiber*, June 1987, Life Sciences Research Office, Federation of American Societies for Experimental Biology, Bethesda, Md). Historically, dietary supplementation has been proposed as an adjunct to conventional drug therapy for numerous diseases including hyperlipidemia, hypercholesterolemia and diabetes. The primary problem associated with successful deployment of these dietary regimes is that appealing foods of sufficient variety are not available to provide sufficient incentive for the patient over time. Many brans or celluloses, i.e. fibers, containing soluble fiber have too high a water regain (i.e, the food becomes mushy) or if not adequately hydrated, contribute gritty texture to the food in which it is incorporated. Soluble gums, for example, commercially available pectin, guar and psyllium, are too viscous when employed at concentrations deemed to be efficacious and dramatically affect the processing and palatability of the food. However, pectins isolated from sugar beet in accordance with this invention have now been found to provide a means of achieving high soluble fiber loading into many food products without substantially changing appearances, texture and taste. Furthermore, these pectins are believed to represent an efficacious source of dietary fiber which may influence hypocholesterolemic, hypoglycemic and hypolipidemic response in humans.

The use of high intensity sweeteners such as aspartame TM, sucralose TM and others to replace nutritive carbohydrates in foods and beverages changes the properties of the product in which they are incorporated. For example, in cakes and cookies sucrose functions as an agent to bind water and serves as an integral component of the solids matrix. In carbonated beverages invert sugar or high fructose corn syrup solids contribute to mouth feel. These properties are lost when high intensity sweeteners are used to replace sugar (often the replacement ratio exceeds 1 part for 200). Since the propose of sugar replacement is to produce a reduced calorie or dietetic food, the functional solids which must be added to replace the nutritive solids displaced by the high intensity sweetener must be of low nutritional value as well as provide appropriate "body" or consistency to the product. Nominally solids replacement can be carried out by substituting a low or no calorie material on a one-for-one basis (i.e., 1 part additive for 1 part sugar replaced). Another method for replacement is to add a material which has a normal calorie index but which provides "body" functionality at a lower use lever (for example, certain polysaccharides with nutritional indexes similar to sugar, i.e. 4 calories/gram, may replace several parts of sugar in a recipe). In practice, some combination of both methods is frequently used. Pectins isolated from sugar beet can provide both properties and it is believed they will find significant use as a solids replacement additives in dietetic foods and beverages. Because beet pectin is largely composed of carbohydrates not digested or utilized by humans (D-galacturonic acid and L-arabinose account for over 70% of organic content), its nutritional index is low — perhaps on the order of 0.5 cal/gram or less. And because beet pectin is a relatively high molecular weight polysaccharide, it is able to achieve viscosities and water binding properties of high solids sugar syrups at concentrations one-fifth to one-tenth that of simple carbohydrates such as sucrose, invert or dextrose. For example, its use in a 12 ounce diet beverage at 2% w/w would contribute on the order of only 2 to 4 calories. It is further believed that the ability of beet pectin to form flexible, non-hygroscopic films on removal of water will promote beneficial texture development in dietetic, baked food products such as breads, cookies and cakes.

As indicated in the parent application Ser. No. 512,940, now U.S. Pat. No. 4,831,127, the entire contents of which is incorporated by reference, sugar beet pectin can be isolated in high yield by thermomechanical extraction of spent beet pulp under mildly acidic conditions. The preferred raw material is wet, pressed spent pulp. Since wet pulp is available only a short period during the year, dried pulp in the form of shreds or pellets may also be employed. Extraction temperatures in excess of 100° C. are preferred with temperatures in the range of 120° to 160° C. even more preferred. Relatively short residence times at these temperatures, typically under 5 minutes are preferred. Discharge to atmospheric pressure is achieved through a small diameter orifice with the jet impacting against a discharge plate. The high shear generated serves to enhance release of pectins and to disperse the processed tissue. The resulting puree containing dispersed cell walls, colloidal matter and solubilized pectins in an aqueous matrix is mechanically separated into a particulate fraction and a solubilized fraction-particulate being all matter retained on a 500 mesh screen and the soluble fraction being all material passing through the 500 mesh screen. Yields of the soluble fraction are functions of the thermomechanical conditions, pH and method of solid/liquid separation employed. Yields are interrelated with desired properties of the pectin isolated. The protopectin material in beet is very complex and depending on the processing conditions more or less of certain fractions are released, admixed and accumulated from between and within the primary cell wall matrix. Therefore, depending on the method of extraction subtle or sometimes dramatic differences in the properties of the pectin may be observed.

Typically pH's in the range of pH 1.0 to pH 4.5 are effective in the preferred temperature range. Adjustment of pH prior to processing may be achieved with any strong mineral acid ($H_3SO_4$, $H_3PO_4$, HCl) with $H_2SO_3$ ($SO_2$ saturated water @ 20° C.) preferred. Alternatively organic acids such as acetic, citric, malic or succinic acids may be used at the upper range of pH. Yields of soluble fraction may range from 25 to 60% w/w based on initial pulp solids. Further refining of the pectin may be desired to remove colloidal matter, reduce color, and de-ash. Drying is achieved by spray drying or thin film technique such as atmospheric drum drying.

According to a most preferred embodiment of the present invention, both hemicellulosic and cellulosic components of sugar beet pulp or other parenchymal cell-containing plant material are isolated essentially simultaneously without substantial degradation of either component. Such may be accomplished through hydrolysis of spent sugar beet pulp (or other plant material containing parenchymal cells in high proportion) under conditions of moderate pH and high temperature for relatively short periods of time in association with physical shearing to improve dispersibility and pectin release.

According to one embodiment of this invention, the acidic extraction of sugar beet pulp is accomplished at pH's below about 4.5 and preferably at pH's below about 4.0 and even more preferable between 4.0 and 2.0. This acidic condition is maintained at a temperature above room temperature and for a period of time which is sufficiently substantial to liberate pectin and arabinogalactan from the sugar beet pulp but which is not sufficient to substantially degrade the same.

It is preferred that a temperature greater than about 125° C. be employed. It is more preferred to employ temperatures from about 125° C. to about 250° C. and even more preferred to employ temperatures between 140° C. and about 200° C. Still other preferred embodiments employ temperatures between about 150° C. and 180° C.

As will be appreciated by those skilled in the art reaction times which are sufficient to liberate hemicellulosic components from sugar beet pulp, pectins and arabinogalactans, will vary depending on the pH employed and the reaction temperature. It is preferred that reaction times less than about 600 seconds be employed. It is still more preferred that reaction times less than about 360 seconds be so employed with a still more preferred range being reaction times below about 200 seconds. In general, reaction times effective to liberate the components will be greater than about 15 seconds and preferably greater than about 30 seconds.

According to one preferred embodiment, sugar beet pulp in aqueous slurry was acidified to a pH of about 3.5 with concentrated hydrochloric acid and hydrolyzed for approximately 40 seconds at 160° C. In accordance with another embodiment, sugar beet pulp was acidified to a pH of about 2.2 with HCl and hydrolyzed for about 170 seconds at about 165° C. As will also be understood by those skilled in the art, wide combinations of pH's, reaction time and temperature will be satisfactory for performing one or more of the embodiments of the present invention.

In consequence of the foregoing analysis, those skilled in the art will appreciate that it is best to define the reaction conditions by what they accomplish rather than by their numerical values. Thus, a sufficient combination of pH, reaction time and reaction temperature which allows the liberation of pectin and arabinogalactan from spent sugar beet pulp (or other parenchymal cell containing plant material) without the substantial degradation thereof is desired. For certain preferred embodiments, it is preferred that such degradation be minimized. For others, a certain degree of degradation may be allowed or even encouraged such as when novel vegetable gums are desired. It is believed that from analysis of the foregoing discussion concerning reaction conditions, one of ordinary skill in the art will readily be able to appreciate those modifications which must be made in the combination of pH, reaction time and reaction temperature to allow the isolation of pectin components, of sugar beet pulp for any particular purpose.

It is believed that the presently indicated combinations of moderately acidic pH, relatively high temperature and relatively short reaction time have not heretofore been suggested for use in connection with parenchymal cell containing material. It is believed that it is this combination of factors which is partly responsible for the isolation of the pectin components of sugar beet pulp without substantial degradation.

The isolation of the pectin components of sugar beet pulp or other parenchymal cell containing plant material may also be accomplished in strongly alkaline conditions. Thus, combinations of high (strongly basic) pH, relatively high temperature and relatively short reaction times may be so employed for such isolation. This combination of stringent pH at high temperatures for short times, however, results in the isolation of hemicellulosic components from such plant materials with substantial hydrolytic degradation, particularly with respect to saponification of ester functionality. In this regard, it is preferred that pH's greater than about 9.0 be employed for this hydrolysis. It is still more preferred to employ pH's between about 9.5 and about 12.0 and even more preferred to employ pH's from 10.5 to about 11.0.

Combinations of pH, time and temperature may be varied by those skilled in the art while not departing from the spirit of this invention. Such persons will appreciate that variations of such parameters may be employed to modify the total output of alkaline solubilized materials to be produced in accordance with this invention and that diverse vegetable gums may be formulated thereby. In accordance with the practice of this invention employing alkaline hydrolysis, conditions of time and temperature are employed which are sufficient to isolate the pectin component. In this regard those skilled in the art will appreciate that the pectin component present will be quickly hydrolyzed under alkaline conditions to salts of pectinic acids. Such pectinic acid materials are also commercially desirable and lead to useful vegetable gums and other materials.

The times and temperatures which are useful for the alkaline hydrolysis in accordance with the present invention are similar to those which are useful for the acid hydrolysis. Thus, temperatures between about 125° C. and 250° C. may be employed. It is preferred that temperatures between 140° C. and about 200° C. be employed while still more preferred are temperatures between about 150° C. and 180° C.

Reaction times less than about 600 seconds are preferred with reaction times less than about 200 seconds being more preferred and reaction times from about 30 to about 120 seconds are still more preferred for certain embodiments. In general, reaction times greater than about 15 seconds are needed.

The acid or alkaline hydrolysis of sugar beet pulp or other parenchymal cell-containing materials to isolate pectin and modified pectin components is greatly facilitated by the employment of physical shearing in connection herewith. It is preferred that extraction be conducted in conjunction with physical shearing to maximize the production of extractable components. In this regard, it is believed that the physical stressing or shearing assists in the disruption of the intracellular organization of sugar beet pulp and facilitates the liberation of the soluble polysaccharide complex. A wide variety of apparatus may be employed to effect such physical shear. Thus, in accordance with the preferred embodiment, a tubular reactor is employed which passes a slurry of parenchymal cell containing material at elevated temperature and pressure and at the desired pH through its length to one or more exit orifices. The slurry is then sprayed or "shot" through the orifice into a region of lesser pressure. This technique which is well known to those skilled in the art in terms of flash evaporation and other processes, provides a source of mechanical shear which is well suited to the practice of the present invention.

Other forms of mechanical shearing may also be employed such as an in-line blender or other device. With certain embodiments, shearing may be accomplished through ultrasonics or through any other technique which serves to effect substantial disruptions of the cellular organization.

It is most convenient to employ physical shearing simultaneously or shortly subsequent to the hydrolysis of sugar beet pulp or other plant material. Thus, the tubular reactor with "blow down" exit orifice is greatly preferred due to consideration of convenience and cost. It is also possible, however, to employ hydrolysis and physical shearing in separate steps. Thus, the plant material may be hydrolyzed under conditions of pH, time and temperature as hereinabove described, and stored under nonhydrolytic conditions prior to, for example, batchwise physical shearing in a blending device. Other modifications of the hydrolysis/physical shearing scheme will also be apparent to those skilled in the art.

A preferred reactor useful for the acidic or alkaline hydrolysis in accordance with one or more embodiments of the present invention comprises a tubular design. Thus, twelve stainless steel or other tubes having approximately ½ inch inside diameter are parallel mounted through a 25 foot length of 12 inch inside diameter pipe and connected in series. Means are provided for introducing steam or other heating source into the outer jacket of the reactor in a controlled fashion so as to provide the desired temperature in the reaction tubes. An input pumping means is also provided for feeding a slurry of pH adjusted plant material into the reactor tubes. The discharge end of reactor tube series is provided with an orifice of small cross-sectional dimension typically ⅛ to ¼ inch. The orifice serves a dual purpose of maintaining internal pressure within the reactor tubes and of providing a high mechanical shearing effect upon the exit product stream when the same is forced therethrough.

In typical hydrolytic reactions in accordance with this invention, pulp is fed to the foregoing tubular reactor at head pressures ranging from about 200 to about 800 pounds per square inch. Superficial linear velocities at the exit orifice have been estimated from about 10 to 100 meters per second. Thus, strong shear forces are encountered at the discharge orifice. The product of the reactor is effectively "flashed" to atmospheric pressure after exit from the orifice and passed to subsequent processing operations.

While numerous reaction protocols may be employed by those skilled in the art for the practice of one or more embodiments of the present invention, in general, a slurry of plant material such as spent sugar beet pulp suspended in aqueous medium is adjusted to the desired pH, either acidic or alkaline and passed through a suitable reaction apparatus such as foregoing tubular reactor. The pH modified slurry is subjected to combinations of temperature and time at a pressure generally above atmospheric pressure. The material is then, in accordance with the preferred embodiment, passed through an exit orifice to atmospheric pressure to effect physical shearing. The resulting material may be viewed as having solid and liquid components. Separation of the solid and liquid material is generally followed by further processing.

As previously indicated, the sugar beet pectins prepared in accordance with the present invention possess properties which distinguish them from pectin previously known, particularly citrus pectin. In practice, the sugar beet pectins of the present invention are distinguished from citrus pectin, apple pectin, or other commercially available pectins, by one or more of the following properties:
(a) low molecular weight;
(b) highly acetylated;
(c) many hydrophobic domains;
(d) ferulic acid content of up to 3% w/w and preferably from about 1 to about 1.5 percent by weight; and
(e) relatively low viscosity at 10% w/w or higher.

In accordance with another embodiment of the present invention, comestibles are provided comprised of sugar beet pectin, which have been found to be extraordinarily useful in a number of aspects of comestible production. Pectin is highly utilitarian for a wide variety of rheological uses and improvements. Such comestibles may be prepared in the form of dispersions, such as emulsions, foams, gels, doughs, and other forms. In this regard, the term "dispersion", as employed throughout the specification and appended claims, is defined generically to include emulsions, foams, gels, doughs, and the like.

All foods are dispersions containing a least one component dispersed within another, the former being referred to as the "disperse phase," the latter as the "continuous phase." Even drinking water falls within this definition as a result of the presence of particles of colloidal size (page 1 in *Colloids in Foods*, E. Dickinson and G. Stainsby, Applied Science Publishers, London and New York (1982). In a similar fashion, liquid honey will also contain particles that are of colloidal size. Sugar, on the other hand, according to this definition, would be classed as a food additive. While it may be considered that there is no practical or logical justification for distinguishing between foods and food additives, this distinction is nevertheless made (page 70 in *Food and Emulsions*, ed. S. Frisberg, Marcel Dekker, Inc., New York and Basel, 1976). Thus, a food is a dispersion that is also a comestible. Not to recognize foods as dispersions overlooks one of their fundamental properties — that which defines them as being thermodynamically unstable and, therefore, requiring the determination of "shelf-life."

It is the disperse nature of foods that gives to them one of their most important properties, that referred to as "texture." Thus, the "yield" (the yielding of the food as one "bites into it"), the shear thinning (such as salad dressings that look thick in the bottle, but seem quite liquid as they flow down the throat), and flavor release from shear thinning are all important results from foods being dispersions, (Pettie, in *Polysaccharides in Foods*), Butterworths, 1979; Sanderson, Prog. Fd. Nutr. Sci 6 (1982) 77–87; Sanderson, in *Gums and Stabilizers for the Food Industry*, Pergamon, 1982; Sherman, same volume).

Foods are usefully categorized into certain functional divisions. However, there is no one system that is recognized as definitive for all concerned. Thus, a marketing person may use categories that are different from those used by the food scientist.

For food technologists and scientists, and often also for marketing or other people concerned with foods, a useful classification, and one used throughout this specification and appended claims, is the following:
(i) food emulsions,
(ii) food foams,
(iii) food batters,
(iv) food doughs, and
(v) other food dispersions.

An emulsion will be further defined as a dispersion which is either an oil (or fat)-in-water or water-in-oil (or fat) emulsion [in most cases herein the use of the term "water" may more appropriately be replaced by "aqueous" thus, indicating that other materials may be dissolved/dispersed therein]. Thus, either the oil (fat), or the aqueous part, may be the disperse phase. Cream, an oil-in-water emulsion, when churned, inverts to become butter which is a water-in-oil emulsion.

A foam is a dispersion of gas particles embedded in a matrix, which, in turn, will also be a dispersion, either of solids in liquid, solids in solids, or an emulsion.

While cake batters are also distinguishable as cake "emulsions" (I. S. Shepherd and R. W. Yoell, in *Food Emulsions ed. S. Friberg Marcel Dekker Inc.*, 1976), it is usually better to define them under "batters" to make a distinction from doughs, the latter having a more viscous texture than the former. A batter may normally be manually stirred with a spoon, or mechanically mixed with beaters, whereas a dough is manually mixed by kneading or mechanically mixed with dough hooks. A dough is also often a food emulsion, if a fat such as shortening has been used as part of the formulation; however, some doughs may be made up only of flour and water, with possibly a leavening agent — thus, the useful distinction of a separate category as dough. In general, a batter is a pourable dispersion in which the disperse phase is composed of various materials often including an oil (fat), protein aggregate, milk solids, starch, spices, and other additives such as fruit pieces, or nuts.

A dough is a moldable dispersion which is too elastic to be considered pourable in the conventional sense (i.e., it takes a comparatively long time to "pour" a dough, and stretching is a more appropriate term than flowing to describe its motion during such "pouring"). The disperse phase of a dough usually includes a starch; it may also include protein aggregates, oil (fat) emulsion particles, milk solids, spices, and other additives such as fruit pieces or nuts. The disperse phase of a dough normally forms a higher percentage of the total recipe than it does in a batter — hence, the more solid-like behavior.

While emulsions, foams, batters and doughs certainly constitute most formulated foods, and in the absence of rigid definitions most natural foods as well, it is obvious that there are foods that do not easily fall into any of these subdivisions and, therefore, "other food dispersions" must be another category. However, it is neither practical, nor is the number of them sufficiently large, to further subdivide this section at this level of definition, without also further subdividing the other categories, as named, as well.

Comestibles in accordance with the present invention may be prepared comprising yolk-containing aqueous emulsions, frozen confections, ice creams, ice milks, frozen toppings, mayonnaise, mayonnaise substitutes, thixotropic condiments, sauces, and a wide variety of other materials. Such comestibles may also be prepared comprising whips, and a whole host of dispersions, emulsions, gels, foams and other materials useful in the food and drug industries. The present invention also provides reconstitutable mixes for preparation of any of the foregoing materials.

A particular, preferred embodiment of the present invention provides comestibles in the form of foams such as albuminous foams, proteinaceous foams, frozen foams, whipped toppings, and a whole host of reconstitutable mixes for such materials and replacements and substitutes therefore. In accordance with yet another embodiment, the sugar beet pectins may be incorporated into batters, doughs, mixes, and the like, in order to improve texture, processability, or other rheological properties.

Another preferred embodiment secures improvements in beverages and the like though the addition of sugar beet pectins thereto. Juices, dairy and non-dairy frozen beverages, concentrates and the like can all benefit.

In accordance with another preferred embodiment, methods for altering a physical or processing property of a comestible are provided comprising an addition to the comestible of an amount sufficient for effecting the alteration by sugar beet pectin. In accordance with other preferred embodiments, the amount of pectin added to the material to effect the alteration is between about 0.01 and about 30% by weight. It is still more preferred to add from about 0.1 to about 5% by weight.

Dietetic or other specialty comestibles may also be prepared in accordance with this invention in view of the fact that sugar beet pectin has a negligible food value and is devoid of fat or cholesterol. Thus, methods for preparing comestibles having reduced caloric content while maintaining commercially acceptable physical and processing characteristics are comprehended by this invention comprising formulating the comestible to include, for example, at least about 0.2% by weight of sugar beet pectins. Similar improvements in the preparation of comestibles to provide such comestibles having reduced lipoprotein or fat levels while maintaining commercially acceptable physical and processing characteristics are also included within the invention. Thus, such comestibles are preferably formulated to include at least about 0.2% by weight of sugar beet pectin.

A number of aging processes in foods derive from migration of molecules within the food product so that local high concentrations occur. If these molecules prefer a crystalline arrangement, then nucleation may occur with subsequent crystal growth often to unacceptable size. For example, in most frozen foods, water forms ice crystals that grow with time, the larger crystals growing at the expense of the smaller crystals: in ice cream this results in the perception of granularity and a loss of creaminess in texture. Another result of ice crystal growth is "freeze dehydration" as water is "robbed" from the non-aqueous components of the product. The freeze dehydration produces changes to the higher levels of structure of polymeric molecules such as proteins and carbohydrates that are present: undesirable textural changes such as toughness in meats result. Considerable efforts in food research go toward finding methods to prevent ice crystal formation, i.e, to promote freezer storage stability. Another similar process is the recrystallization of starch molecules that results in staling of bread and structural changes in starch gels: this occurs at non-refrigerated storage temperatures. Similarly, sugar forms crystals: this is often noticeable in frozen products, particularly for those where sugar level is relatively high, such as butter tarts.

One embodiment of this invention is the discovery that sugar beet pectin impedes the development of the above ageing processes so that ice cream creaminess is prolonged during storage, and bread maintains a fresh elastic loaf texture for longer periods of time. To achieve such prolonged storage stability improvement, comestibles are preferable formulated to include at least about 0.1% by weight of sugar beet pectin.

In accordance with certain embodiments of the present invention, more complex mixtures may be added to, or included in foods of the present invention in order to improve them. Thus, sugar beet pectin may be co-isolated with certain cellulosic components of the materials from which it is derived. Thus, sugar beet pulp, citrus pulp or other parenchymal cell containing material may be treated in such a way as to co-isolate both parenchymal cell cellulose (PCC), and pectin components of those plant materials. The resulting, combined materials may be useful for any of the methods, and in any of the materials discussed above under appropriate circumstances. Thus, the sugar beet pectin components of such blends, mixtures or co-isolates form a natural gum having properties not unlike naturally-occurring gums well known to persons of ordinary skill in the food science art.

In accordance with one or more embodiments of the present invention, sugar beet pectin can be added to comestibles including foods, other than fruit spreads, in varying amounts for varying purposes. In general, however, amounts of the sugar beet pectin between about 0.1% and about 30.0% by weight of the total has been found to be useful. It is more preferred that amounts of the sugar beet pectin between about 0.2% and about 10% by weight be included with amounts between about 1.0% and 5.0% being still more preferred. Persons of ordinary skill in the art will appreciate that varying amounts of the sugar beet pectin will be appropriate for varying functional uses. Thus, for the stabilization of an oil-in-water emulsion, such as the improvement of artificial mayonnaise and ice creams, certain thixotropic condiments and the like, can benefit from inclusion of from about 0.1% and about 30% of sugar beet pectin by weight of the total. Even more preferred is the inclusion of from between about 0.2% and about 10% of pectin in such materials with additions between about 1.0% and about 5% by weight being still more preferred.

The improvement of comestible foams or froths such as air-in-liquid (e.g., whipping cream, whipping cream substitutes and other whipped materials) can benefit from the inclusion of the sugar beet pectin therein. Thus, amounts between about 0.1% and 20% by weight are preferably used. Even more preferred are amounts between about 0.2% and 10% by weight with addition of between about 0.5% and about 5% by weight being still more preferred.

In accordance with yet another embodiment, the sugar beet pectin is added to batters, doughs and other bakeable material. In such cases, the sugar been pectin improves the structure, body and physical properties of such batters or doughs lending stabilization and improved viscous behavior while imparting very little nutritive value. Amounts of the sugar beet pectin between about 0.1% and about 20% may be added with amounts between about 0.5% and about 10% being still more preferred. In general, the sugar beet pectin may be added to foods in many forms and formulations. Thus, it may be added to improve the qualities of gels, sols, aerosols, foams, emulsions and, generically, dispersions of all types. The exemplary material which follows sets forth numerous embodiments for the inclusion of the sugar been pectin in comestibles. Many others will be apparent to persons of ordinary skill in the art.

A range of products will benefit by use of sugar beet pectin. Some of these are:

1. Dairy Products: Viscosity control, smooth texture, and fat mimicry are all enhanced with sugar beet pectin. Of special interest would be dairy products with textures such as yogurt, milk shakes, custards and ice creams. The structure building capability of sugar beet pectin would make possible low calorie formulas: the combination of low required levels and relatively low cost of sugar beet pectin would have significant cost advantages over the materials presently in use for such purposes. Ice creams are oil-in-water emulsions where the fat is provided by dairy cream: either the dairy proteins or added egg proteins provide emulsification and stabilization. A smooth creamy mouthfeel is partially provided by the emulsified fat droplets. Ice milks which are deficient in the fat phase tend to be less than smooth and less creamy unless other smootheners are added. Smoothness and lightness of texture are enhanced by incorporation of air during freezing of the ice cream and, therefore, "overrun" is normally desirable. The modified sugar beet pectin is demonstrated as a partial replacement for dairy cream whereby it may aid in achieving adequate overrun, and/or in providing rich creamy texture.

2. Pourable Dressings: Emulsion stability and flow/cling properties are all enhanced with sugar beet pectin. Moreover, greater reduction of oil should be easily attained for calorie reduced recipes than is presently possible, while maintaining desirable cling and mouthfeel lubricity.

The data of this study suggest that sugar beet pectin would make an excellent material on which to base no-oil salad dressing formulations. Levels of 1.0-5.0% (perhaps with approximately 0.1% of another hydrocolloid added to achieve a range of cling and mouthfeel properties) should be adequate for such purposes.

3. Puddings and Desserts: The texture of desserts is attained with a gelling agent. "Cold sets" are derived mostly from gelatin, "heat sets" mostly from starch. To get a range of yield values (the initial "bite," smoothness and "thickness") particulate "fillers" are added - these may be no-fat-dry-milk (NFDM) solids, microcrystalline cellulose (MCC), or emulsified fat droplets. Calorie reduction, texture manipulation, and cost reduction would be some of the advantages derived from the use of sugar beet pectin in dessert products.

4. Whipped Products: Stable aerated products are attained through the use of materials that produce a stabilizing elastic structure surrounding the air globule. Thus, in whipped cream, aggregated fat globules intermingle with protein complexes to provide an elastic structure about the fat globules. In meringues, the structure is provided by protein aggregates — heating at a sufficiently high temperature immobilizes the structure by producing an irreversibly entangled protein matrix on a film like encasement. Sugar been pectin has great potential in stabilization of foamed products.

5. Meat Emulsions: These constitute another important class of food products. These emulsions use comminuted meat products and are essentially oil-in-water emulsions. The meat proteins that dissolve in the aqueous phase behave as emulsifiers. Moreover, these proteins aid in the heat effected gelation process that normally is used to bind the product together as a cohesive unit. During the cooking process, loss of liquid can be extensive resulting in "yield loss" with aesthetically undesirable shrinkage. Sugar been pectin helps to prevent this "yield loss."

6. Confectioneries: It would seem that the sugar beet pectin should find use in certain candies as a means to reduce calorie levels. The pectin will also make a good filler for low calorie cake icings.

7. Spreads: Spreads are either dispersions of solid particles in a liquid phase, an emulsion where either the fat/oil, or the aqueous phase, may be continuous, or a combination of both. Stabilization of these products is provided by emulsifiers and/or thickeners (e.g., hydrocolloids). High aqueous phase content is a means of providing low calorie products: however, achievement of adequate product stability becomes more difficult at high water contents. In order to function as a spread, spreadability is an important property and the product must, therefore, be malleable and soft, while thick enough in texture to retain shape. The sugar beet pectin is able to provide stable, creamy and spreadable dispersions when used in certain formulations.

Overall, the sugar been pectin has potential for many functional applications in foods. In addition to the following specific examples, the sugar beet pectin can also be used with positive results as a thickener in jams and other spreads; as a textural enhancer, or as a partial flour replacement in breads and other cakes; as an aid for extrusion of doughs and of cereals; as a stabilizer and/or as a textural enhancer for ice creams, salad dressings, etc.; as a suspension aid, stabilizer, and textural enhancer in beverages such as egg nogs, milk shakes, chocolate milk, etc.; as a thickening agent in cooked puddings and instant puddings; as a foam stabilizer in other fat based "whips," protein stabilized foams (e.g., marshmallows, artificial whipped creams, etc.), or other foams used as foods; to provide stability during storage and ease of use for such convenience commodities as prepared cake icings, instant drinks, packaged spreads, etc.; as an aid for frozen meats and fish to avoid deterioration during storage and to improve working performance; as an aid to prevent scorching during cooking of materials such as puddings which contain starch, or other ingredients having a tendency to scorch. Not only does the sugar beet pectin perform where other materials have become "standards," but it also performs in a more acceptable manner, and in a manner that is unanticipated by an understanding of the existing art.

The following example for the preparation of a useful pectin extract from sugar beet pulp should be considered exemplary and it will be appreciated by one skilled in the art that variations will be necessary or even desirable to achieve the wanted functionality. No additive pulp (pulp without added molasses, Steffen solids or other material) was ground to 30 mesh and hydrated by suspension in hot water at a solids content of 8-10% w/w. Sufficient $H_2SO_3$ was added to adjust the pH to pH 3.5. The swollen pulp slurry was pumped through a proprietary plug flow reactor (manufactured by St. Lawrence Reactors, Ltd., Mississauga Ontario, Canada) at 155° C. The residence time was 40 seconds and the processed mass discharged to atmospheric pressure through a 0.125 inch diameter orifice against an impact disc. The resulting puree was converted into a liquid fraction containing 2.5 to 5.5% non-volatile solids and a sludge fraction employing a belt press (manufactured by Perrin Ltd., Toronto, Ontario, Canada). The sludge is discarded. The liquid fraction may be further refined by conventional centrifugation, filtration, decolorization, evaporation and spray dried. A preferred method involves centrifugation and concentration of the clarified supernatant by ultrafiltration. Subsequent dia-filtration employing a 30,000 Dalton cut-off membrane removes low molecular weight components prior to spray drying. The resulting powder is free flowing and non-hydroscopic, rehydrating on addition of water.

Typically the pectins obtained by the above procedure have a proximate analysis of 95% non-volatile matter containing 2-10% w/w ash on total solids. Refined material which has been decolorized is an off-white powder which hydrates to a pale yellow or amber solution depending on the concentration. The carbohydrate profile after acid and enzymatic hydrolysis is 40 to 75% w/w D-galacturonic acid eluting substances (D-rhamnose and D-galacturonic acid coelute in the HPLC system employed), 15 to 25% w/w L-arabinose and 5 to 10% w/w D-galactose. Acid insoluble matter on extensive acid hydrolysis (presumed to be feruloylic acid) is typically less than 3% and generally ranges 1 to 2% w/w. Protein content was estimated at 6.25 times Kjeldhal nitrogen and is typically under 1%. The degree of esterification, both acetyl and methyl ester) is highly variable depending on the degree of processing employed. For the above example, the degree of acetylation expressed as acetic acid content is 5.3% w/w and the methyl ester expressed as methanol is 3.8% w/w (determined by GC of an alkaline saponified sample). The rheology of a 10% solids solution likewise varies significantly depending on the degree of processing. Using a Bohlin 88 viscometer, (Bohlin Reologi Inc., East Brunswick, N.J.), a 10% w/w solution appears somewhat pseudoplastic and displays a finite yield point employing the Casson model (for example, viscosity is 154 mPa.s at 1200 sec.$^{-1}$ versus 257mPa.s at 1 sec.$^{-1}$ with an apparent yield point of 359 mPa). Apparent yield points have been obtained in excess of 10,000 mPa for sugar beet pectin preparations which have been enriched with the higher molecular weight components by ultra and dia-filtration. It will be appreciated by one skilled in the art that the molecular weight profile and various degrees of substitution and branching of the macromolecular components constituting that profile, will determine the in vitro rheological properties and in situ interactions with fats, oils, proteins and other components found in food products; moreover, these functional characteristics will be determined by the degree and kind of processing employed for the isolation of sugar beet pectin.

The following examples are illustrative of the invention:

EXAMPLE 1

FLAVOR OIL EMULSION STABILIZATION

Brominated vegetable oil ($\sigma=1.334$) and California orange oil ($\sigma=0.844$) were obtained from Felton International, Inc. of Toronto, Canada. Purity Gum TM (an octenyl succinate derivative of starch), manufactured by National Starch Company, was also obtained from Felton. Gum arabic was obtained from Sigma Chemical Company, St. Louis, Mo. Other chemicals were reagent grade from various chemical suppliers. A mixture of orange oil (5.05 parts by weight) and brominated vegetable oil (4.95 parts by weight) was prepared. The measured specific gravity was 1.046. Master emulsion bases were prepared in tap water for Purity Gum TM at 10% w/w pH 4.36, gum arabic at 5% w/w pH 5.46 and sugar beet pectin (HC-223) at 5% w/w pH 4.5 containing 0.1% w/w sodium benzoate. A 10% w/w flavor oil in water emulsion was prepared by homogenization of a 250 g mixture (225 g base and 25 g oil) for six minutes at 10,000 rpm employing an Ultra Turax TM T50 homogenizer with a G40F generator assembly (manufactured by IKA Laboratories of Staufen, West Germany). The temperature rise did not exceed 47° C. and the homogenates were quickly cooled to room temperature. Examination under the light microscope indicated all homogenates contained a dispersed phase under $5\mu$ and most droplets were under $2\mu$. All three homogenates appeared similar in particular size distribution. A master beverage base was prepared containing:

240 g sucrose
20 g citric acid monohydrate
2.0 g sodium benzoate
1738 g water

The pH of the beverage base @20° C. was 2.48 and the $\sigma=1.052$. An aliquot of each master emulsion (3.1 ml) was introduced into 200 ml of the beverage base in a capped 250 ml Erlenmeyer flask and well dispersed by shaking. All three emulsions produced a milky white, homogeneous dispersion on mixing with the beverage base. After 24 hours at 20° C., both the master and beverage emulsions were stable and homogeneous. The pectin stabilized emulsion was indiscernible from that of gum arabic and modified starch. After three months some gravitational sedimentation occurred in all three emulsions, both master and beverage. The homogenization device either evaporates away sufficient volatile orange oils (or they become solubilized over time) to cause the density of the oil mixture to increase causing perhaps the larger particle population to gravitationally settle. In all three cases, the settled particles did not coalesce and were completely redispersed by simply swirling or shaking the container. While in practice this phenomenon would not be desirable (and would be eliminated by proper formulation and reduction in the size of the oil droplet population), it is a severe test for emulsion stability in that the settled emulsion droplets are in intimate contact yet do not coalesce.

EXAMPLE 2

Carbonated Beverages

Carbonated beverages in which a high intensity sweetener was substituted for sucrose were prepared from flavor emulsions stabilized with sugar been pectin. A control containing 0.1% w/w CMC, which is commonly employed as an agent to restore "mouth feel" lost by the removal of sucrose solids, was compared with a beverage containing only the pectin carried over from the master emulsion. In addition, a beverage was prepared containing relatively high amounts of pectin at 2% w/w, demonstrating that a highly palatable "high fiber", carbonated beverage could be formulated which would have very low caloric content, yet deliver a high amount of soluble fiber per 12 oz. serving (7 g soluble vegetable fiber).

Sucralose ™, a trichloroglactosucrose derivative, was obtained from Redpath Industries, Toronto, Canada, and prepared as a 10% w/w aqueous solution. Low viscosity CMC (sodium carboxy methyl cellulose), was obtained from Sigma Chemical Company, St. Louis, Mo., and the flavor/weighting oils from sources identified in the previous example. All other reagents were certified, or food grade obtained through commercial vendors.

The master flavor emulsions were prepared by homogenizing a 10% w/w oil mixture $\sigma = 1.0$ (1.146 parts orange oil, $\sigma = 0.844$ with 0.854 parts BVO, $\sigma = 1.33$) containing 10% w/w sugar beet pectin. Initial homogenization was performed by high speed dispersion employing a rotor/stator device at 20,000 rpm, Omni International, Waterbury, Ct., and a secondary homogenization with an ultrasonic dismembrator obtained from Fisher Scientific Company, Chicago, Ill. Table I lists the composition of the final beverages.

TABLE I

| | CMC Expt. | Control | High Fiber Expt. |
|---|---|---|---|
| Water | 970.40 g | 971.49 g | 951.49 g |
| Sucralose ™ 10% w/w | 1.29 g | 1.29 g | 1.29 g |
| Citric Acid monohydrate 50% w/w | 5.44 g | 5.44 g | 5.44 g |
| Sodium Citrate dihydrate | 4.42 g | 4.42 g | 4.42 g |
| 25% w/w Sodium Benzoate | 1.76 g | 1.76 g | 1.76 g |
| 15% w/w CMC | 1.09 g | — | — |
| Sugar Beet Pectin (247/248) | — | — | 20.0 g |
| Flavor Emulsion 10% w/w | 15.6 g | 15.6 g | 15.6 g |
| | 1000.0 | 1000.0 | 1000.0 |

Carbonation was achieved by addition of 2.5 g dry ice to 200 g of beverage in a standard, long neck clear glass beer bottle (total internal volume 382 ml) and capping. After sixteen hours, the $CO_2$ equilibrated without leaking around the cap seal producing a well carbonated beverage on uncapping.

After ten days, all three beverages displayed excellent emulsion stability with no visual evidence of ringing or settling. On opening, the CMC containing beverage was undiscernible by taste and mouth feel from the control containing pectin carried over in the master flavor emulsion. Note the approximate 60× dilation of the 10% w/w pectin in the emulsion results in a 0.17% w/w pectin component in both the control and CMC (0.1% w/w) containing beverage which indicates that pectin is dominating the mouth feel of both beverages. The 2% w/w pectin beverage had a pleasant, but pronounced body, and appeared to slightly mute the orange flavor indicating its potential use as an agent controlling flavor release in beverages or other comestibles. All three types of beverage showed no evidence of degeneration after storage at room temperature, or refrigerated at 4° C. for four months. A small amount of emulsion settling was observed, but no coalescence was observed and the emulsion was easily restored by gentle agitation.

EXAMPLE 3

Pumpable Vegetable Oil Spreads

The objective of this example is to produce a reduced caloric margarine spread that is pumpable and can be conveniently dispensed from a container by squeezing or metering via the "toothpaste or lotion" type pump container. It has been found possible to form a stable high oil content (>50% oil) in water emulsion with beet pectin whereby the emulsion is formed at a temperature above the melting point of the oil/fat phase. The resulting emulsion is then cooled to a temperature below the melting point of the oil/fat phase but above the freezing point of the continuous phase to produce a hardened non-coalescing suspension of the oil/fat phase.

A 175 g aliquot of ordinary margarine (non-salted 80%, hydrogenated soya oil based, containing 40% polyunsaturates) was added to 105 g of an aqueous sugar beet pectin syrup (HC-223, 13.6 brix, pH 4.5) and heated to 50° C. The binary mixture was homogenized for three minutes on the Ultra Turax at 10,000 rpm. The final calculated composition of the homogenate was 5.1% w/w beet pectin solids (13.6% w/w based on aqueous continuous phase), 32.3% w/w water and 62.5% w/w margarine. The viscous homogenate was poured into a "hand lotion pump" container and placed in the refrigerator overnight at 4° C.

On examination the next day the gel-like homogenate was pumpable and showed no signs of coalescence. After 2.5 months, the mixture showed no visible change and was pumpable yielding a creamy white gel that is readily spreadable. It is clear that the pectin emulsion under these conditions results in a gel-type structure, which although sufficient in strength to prevent buoyant creaming of the lighter fat/oil phase, is easily broken to allow flow to occur.

EXAMPLE 4

Incorporation of Soluble Fiber into White Bread

It has been found that the pectin isolated from sugar beet can be added to breads in significant quantity without changing the apparent dough handling properties or appearance and texture of the final baked bread. The following recipes were used:

|  | Control Bread | Experimental Bread |
|---|---|---|
| Generic bleached flour (3 c.) | 420 g | 420 g |
| Salt (1 tsp.) | 9.0 g | 9.0 g |
| Sugar (1 tblsp.) | 12.0 g | 12.0 g |
| Scalded skim milk (1 c.) | 233.0 g | |
| Cooled to 40° C. (¼c.) | 56.0 g | |
| Beet pectin sol. @ 12% bx. (1 c.) | | 260.0 g |
| Warmed to 40° C. (¼c.) | | 62.7 |
| 1 pkg. yeast | 7.0 g | 7.0 g |
| Margarine (2 tblsp.) | 28.0 g | 28.0 g |

The yeast used was Fleischman's Rapid Rise TM and other ingredients generic grocery products. All ingredients with the exception of the flour were well mixed on a Sunbeam Mixmaster TM. Flour was gradually added employing dough hooks and mixed for four minutes at high speed. The resulting dough was removed and hand kneaded for a further four minutes. Additional flour was added during hand kneading to control the sticky character of the resulting doughs in amounts of 27.1 g and 30.4 g for the control and experimental doughs, respectively. The doughs were allowed to rise at 80° F. in a high humidity environment — first rise was 1 hour and 15 minutes for both; second rise was 2 hours 10 minutes for control and 1 hour 50 minutes for the experimental loaf. Both breads were baked at 350° F. for 45 minutes.

The baked loaves were very similar in loaf volume and weighed 627.5 g (control) and 670.6 g (experimental). The difference is largely a consequence of the added pectin solids and the slightly larger addition of flour during kneading. The amount of beet pectin added amounts to 38 grams or nearly 9% based on flour content. If a 20 slice loaf is assumed, the soluble dietary fiber content is approximately 2 g/slice and is achieved without significant change in texture, color, taste or quality in general of the final loaf.

EXAMPLE 5

Encapsulation of Oleaginous Materials — Vitamin E

Two types of beet pectin were prepared. The first (HC-237), was prepared employing an 86 second reaction time at pH3.5, 60° C, using never dried spent pulp. It was refined by centrifugation, concentrated and dialyzed by microfiltration against a 0.45µ highly anionic membrane to approximately 15 brix. It represents a low viscosity pectin giving an apparent yield point of 13 mPa and a viscosity of 27 mPa.s at 1200 sec$^{-1}$ at a concentration of 10% w/w, pH 4.5. The second preparation HC-P268/274 was prepared by ultrafiltration (30,000 Dalton membrane) of the microfiltration permeate from a standard mild extraction, pH3.5, 38 sec at 160° C. It represents a low molecular weight population of pectins normally discarded during membrane based processing, and forms thickened, but pourable syrups at 40% solids. Both pectin preparations are excellent film formers.

Two types of systems are commonly employed when spray drying is the means of encapsulation. The first employs an emulsion stabilizing agent, typically a hydrophobically modified starch such as Amiogum TM, in conjunction with a high solids carrier which provides film forming function such as a 10 DE maltodextrin. The second employs a single agent as both stabilizer and carrier, such as gum arabic or Capsul TM, an octenyl-succinate derivative of hydrolyzed starch. Each of the two pectin preparations described above represents one of the two types of encapsulation systems — HC237, a natural stabilizer, can be supplemented with an inexpensive maltodextrin carrier similar to Amiogum TM, or HC-P268/274, provides an all natural, high solids combination stabilizer/carrier similar to Capsul TM or gum arabic.

System 1: A 40% w/w total solids emulsion of α-dl tocopherol acetate (Vitamin E), obtained from Hoffman La Roche, Nutley, N.J., was prepared by homogenization of one liter for 15 minutes of a 19.7% w/w neat Vitamin E oil in a 20.9% w/w pectin syrup (HC-P263/274) pH 3.4 at 66° C. employing a rotor/stator type homogenizer (Model CJ4B, ARDE Berinco, Mahwah, N.J.). The homogenate was then spray dried in a Bowen Model JBE926 laboratory sprayer employing an inlet temperature of 400° C. and an outlet temperature of 260° C. The resulting product was a light tan, free flowing powder with a bulk density of 0.27 and particle size distribution largely between 200 and 600µ (70% 600-425µ) and assayed by GC at 47.6% vitamin E on an "as is" basis, or on a "dry basis" (12 hrs. at 80° C.) was 48.5% dry basis. Calculated content is 48% Vitamin E.

System 2: A 57% w/w total solids emulsion was prepared by homogenizing sufficient Vitamin E oil into a 12.9% w/w pectin syrup (HC 237), containing 27.1% w/w maltodextrin to a final concentration of 28.6% w/w oil, 19.4% w/w maltodextrin and 9.2% w/w pectin. The temperature of the resulting homogenate was 65° C. and the pH 3.9. Sufficient water was added (175 ml to 980 g of homogenate) to thin the mixture for spray drying at a final solids content of approximately 50% w/w. Homogenization and spray drying parameters were similar to those described in System 1. A free flowing, off-white powder, with a specific gravity of 0.26 was obtained. The majority of the particles were in the 200-600∞ range (71% 425-600µ). The Vitamin E content was determined to be 42.7% on an "as is" basis, and on a "dry basis" was 43.5% dry basis. The expected content is 50% Vitamin E.

EXAMPLE 6

Hypocholestrolemic Response in Rate to Dietary Cholesterol Challenge in the Presence of Beet Pectin While it is acknowledged that substantial difference exists between rat and human metabolism, the rat model is considered to be a potential indicator of agents influencing cholesterol transport, storage and metabolism in mammals. The rat model is particularly interesting because this animal is believed to have very little control over cholesterol absorption in the gastrointestinal tract. smaller livers (both in real weight or percentage of body weight).

TABLE 2

|  | Diet B | Diet BC | Diet 5F-BC 5% Fiber | Diet 10F-BC 10% Fiber |
|---|---|---|---|---|
| Animal Starting wt. (g) | 185 ± 4.4 | 185 ± 3.4 | 185 ± 5.6 | 185 ± 5.4 |
| End wt. (g) | 332 ± 11.8 | 327 ± 7.4 | 318 ± 9.8 | 322 ± 9.1 |
| D wt. (g) | 147 ± 7.7 | 142 ± 6.5 | 133 ± 7.1 | 137 ± 5.3 |
| Liver wt. (g) | 9.7 ± 0.57 | 13.0 ± 0.67 | 11.9 ± 0.59 | 11.5 ± 0.59 |
| Rel. liver wt. (%) | 2.91 ± 0.08 | 3.96 ± 0.14 | 3.74 ± 0.10 | 3.59 ± 0.03 |
| Serum (mg/dl) | | | | |
| Total Cholesterol | 5.4 ± 2.02 | 60 ± 1.27 | 57 ± 1.79 | 55 ± 1.91 |
| % HDL Cholesterol | 51.8 ± 1.86 | 49.6 ± 1.01 | 48.9 ± 2.18 | 49.3 ± 1.42 |
| Triglycerides | 42.7 ± 1.8 | 42.3 ± 1.6 | 43.3 ± 2.6 | 44.7 ± 3.1 |
| Liver Analysis (g)/100 g | | | | |
| Total Cholesterol | 0.674 ± .016 | 2.54 ± 0.32 | 2.29 ± 0.22 | 2.15 ± 0.21 |
| Free Cholesterol | 0.250 ± .015 | 0.476 ± .018 | 0.475 ± .007 | 0.439 ± .033 |
| % Ester Cholesterol | 62.9 ± 1.65 | 80.0 ± 2.31 | 78.4 ± 1.93 | 78.4 ± 2.88 |
| Triglycerides | 2.526 ± 0.43 | 7.82 ± 0.75 | 7.41 ± 0.77 | 7.36 ± 0.83 |
| Serum Cholesterol | | | | |
| (pool) (mg) | 5.4 ± 0.33 | 5.8 ± 0.20 | 5.5 ± 0.23 | 5.3 ± 0.24 |
| Liver Cholesterol (mg) | 65.5 ± 5.0 | 331.1 ± 47.9 | 272.4 ± 29.6 | 243.0 ± 20.9 |
| Serum + Liver Cholesterol (mg) | 70.9 ± 5.2 | 337.0 ± 48.1 | 276.0 ± 29.7 | 248.4 ± 20.8 |

Alternatively, the rat maintains serum cholesterol and related circulating conjugate levels very well with the result that excess is accumulated by the liver. Therefore, liver cholesterol loading is believed to be a measure of the effectiveness of agents incorporated into the diet, which influence reabsorption of secreted cholesterol (bile acids) and dietary cholesterol (ingested).

Male Wistar rats were purchased from the Charles River Breeding Labs, Wilmington, Mass. Four groups of six rats were acclimated for seven days on a standard semi-purified diet manufactured by Dyets Inc., Bethlehem, Pa. to a specification similar to that employed in conventional nutritional studies reported by others (Kritchevsky, D. et al, "Serum & Liver Lipids of Rats Fed Coco Butter, Corn Oil, Palm Kernal Oil, Coco Oil and Cholesterol", Nutrition Research, Vol. 8, pgs. 287-294 (1988)). After the acclimation period, the four groups of rats were separated and received the following diets.

Diet B — basal diet (control group).
Diet BC — basal diet and 5% cholesterol.
Diet 5F-BC — basal diet and 5% cholesterol +5% sugar beet pectin.
Diet 10F-BC — basal diet +5% cholesterol +10% sugar beet pectin.

The sugar beet pectin preparation had been prepared by a mild acidic extraction —pH 3.5, 38 sec. residence time at 160° C. using dried spent pulp. It had been clarified by centrifugation, concentrated and dialyzed by microfiltration, and spray dried to a fine, light tan powder. The rheological profile of a 10% w/w solids solution at pH 4.5 gave an apparent yield point of 2300 mPa and a viscosity at 1200 sec$^{-1}$ of 243 mPa.s indicating a moderately viscous fluid. The degree of methyl esterification based on the galacturonic acid content was 80%. It was blended into the basal diet in powdered form.

After 21 days the rats were sacrificed. Serum was taken for analysis of cholesterol and triglycerides. The liver was examined for total and free cholesterol and triglycerides. Key organ weights and total subject weights were recorded. Table 2 summaries the results. No animals showed any effects of nutritional distress. The fiber diet did not affect body weight, but led to As expected, sugar beet pectin had little effect on reduction of serum lipids, but did cause reduction of 10 to 15% in total liver cholesterol. The serum plus liver pools in the 5% and 10% pectin groups were reduced by 18 and 26%, respectively, compared to the control cholesterol group. Based on these studies, sugar beet pectin appears to have a low, but significant, effect on cholesterol absorption in the rat model. This indicates it may be effective as a soluble dietary fiber supplement in human diets, augmenting or replacing other fiber ingredients to provide an important dietary function without severe organoleptic distress of foods into which it is incorporated.

Although the invention has been illustrated by the preceding examples, it is not to be construed as being limited to the materials employed therein, but rather, the invention is directed to the generic area as herein before disclosed. Various modifications and embodiments of the invention can be made without departing from the spirit or scope thereof.

What is claimed:

1. Sugar beet pectin having at least one of the following properties:
    (a) low molecular weight;
    (b) highly acetylated;
    (c) many hydrophobic domains;
    (d) ferulic acid content up to about 3% by weight; and
    (e) relatively low viscosity at about 10% by weight
said sugar beet pectin having been prepared by:
    suspending sugar beet plant material in an aqueous medium to form a suspension;
    adjusting the pH of said suspension to a value less that about 4.5 or greater than about 9.0;
    maintaining said suspension at a temperature greater than about 125° C. for from about 15 to about 600 seconds;
    subjecting said suspension to mechanical shearing; and
    isolating said sugar beet pectin from said suspension.

2. Sugar beet pectin of claim 1, which is retained by a 30,000 Dalton ultra-filtration membrane.

3. Sugar beet pectin of claim 1, containing at least about 30% and up to about 60% by weight of galacturonic acid.

4. A food or drug comestible, other than fruit spreads, having at least one of the following properties:
 (a) reduced caloric content;
 (b) reduced fat content;
 (c) improved texture;
 (d) improved flavor release; or
 (e) improved mouthfeel;
said comestible being comprised of at least one first material, at least one second material, and the sugar beet pectin of claim 1 in an amount sufficient to input at least one of said properties to said comestible.

5. The comestible of claim 4, which is a food product.

6. The comestible of claim 5, wherein said food product is at least one member selected from the group consisting of emulsions, foams, batters and doughs.

7. The comestible of claim 6, wherein said food product is an emulsion.

8. The comestible of claim 7, wherein said emulsion is a liquid-in-liquid emulsion.

9. The comestible of claim 8, wherein said emulsion is an oil-in-water emulsion.

10. The comestible of claim 8 wherein said emulsion is a water-in-oil emulsion.

11. The comestible of claim 6, wherein said food product is a foam.

12. The comestible of claim 11, wherein said foam is comprised of a gas and at least one liquid.

13. The comestible of claim 11, wherein said foam is comprised of a gas and at least one dairy product.

14. The comestible of claim 11, wherein said foam is a whipped cream product and is prepared from at least one dairy product.

15. The comestible of claim 11, wherein said foam is a whipped cream product and is prepared from at least one non-dairy product.

16. The comestible of claim 6, wherein said food product is a batter.

17. The comestible of claim 6, wherein said food product is a dough.

18. The comestible of claim 4, which is a drug.

19. The comestible of claim 4, which contains parenchymal cell cellulose in addition to sugar-beet pectin.

20. A dietetic food or drug comestible other than fruit spreads, comprised of said comestible and the sugar beet pectin of claim 1 as a low caloric bulking agent.

21. A dietetic food drug comestible other than fruit spreads, comprising of a dairy or non-dairy product and the sugar beet pectin of claim 1 as a fat-sparing agent.

22. A food or drug comestible, other than fruit spreads, comprised of said comestible the sugar beet pectin of claim 1 as a soluble fiber.

23. A process for imparting to a food or drug comestible, other than fruit spreads, at least one of the following properties:
 (a) reduced caloric content;
 (b) reduced fat content;
 (c) improved texture;
 (d) improved flavor release; or
 (d) improved mouthfeel;
said comestible being comprised of at least one first material dispersed in at least one second material, which process comprises admixing with said food or drug comestible sugar beet pectin in an amount sufficient to impart at least one of said properties to said food or drug comestible.

24. The process of claim 23, wherein oleaginous food additives are encapsulated with said sugar beet pectin.

25. The process of claim 23, wherein foams are stabilized with sugar beet pectin.

26. The process of claim 23, for preparing emulsions containing sugar beet pectin.

27. The process of claim 23, wherein sugar beet pectin is added as a low caloric bulking agent.

28. The process of claim 23, wherein sugar beet pectin is added as a fat-sparing agent.

29. The process of claim 23, wherein sugar beet pectin is added to provide a soluble fiber for the control of cholesterol.

* * * * *